United States Patent [19]
Nordman

[11] Patent Number: 5,833,826
[45] Date of Patent: Nov. 10, 1998

[54] METHOD AND APPARATUS FOR REDUCING THE DISTORTION OF A SAMPLE ZONE ELUTING FROM A CAPILLARY ELECTROPHORESIS CAPILLARY

[75] Inventor: Eric S. Nordman, Palo Alto, Calif.

[73] Assignee: The Perkin-Elmer Corporation, Foster City, Calif.

[21] Appl. No.: 766,009

[22] Filed: Dec. 13, 1996

[51] Int. Cl.[6] .......................... G01N 27/26; G01N 27/447
[52] U.S. Cl. .......................... 204/452; 204/451; 204/601; 204/603
[58] Field of Search ...................... 204/601, 602, 204/603, 604, 605, 451, 452, 453, 454, 455

[56] References Cited

U.S. PATENT DOCUMENTS

| | | | |
|---|---|---|---|
| 5,073,239 | 12/1991 | Hjerten | 204/453 |
| 5,141,609 | 8/1992 | Sweedler et al. | 204/603 X |
| 5,439,578 | 8/1995 | Dovichi et al. | 204/603 |
| 5,529,679 | 6/1996 | Takahashi et al. | 204/663 |

*Primary Examiner*—Kathryn L. Gorgos
*Assistant Examiner*—John S. Starsiak, Jr.
*Attorney, Agent, or Firm*—Paul D. Grossman

[57] ABSTRACT

An electrophoresis system including means for reducing the distortion of a sample zone eluting from a capillary electrophoresis separation capillary is disclosed. The system includes one or more separation capillaries, each separation capillary having an inlet end and an outlet end; a first electrode in electrical communication with the inlet ends of the separation capillaries; a second electrode in electrical communication with the outlet ends of the separation capillaries; and one or more focusing electrodes in electrical communication with the outlet ends of the separation capillaries. In operation, the voltage of each of the electrodes is adjusted such that (i) the sample zone is transported from the inlet end to the outlet end of the separation capillaries and (ii) the distortion of the sample zone eluting from the separation capillaries is reduced.

9 Claims, 6 Drawing Sheets

METHOD AND APPARATUS FOR REDUCING THE DISTORTION OF A SAMPLE ZONE ELUTING FROM A CAPILLARY ELECTROPHORESIS CAPILLARY

FIELD OF THE INVENTION

This invention relates to an electrophoresis method and apparatus for practicing the method. More specifically, this invention relates to a capillary electrophoresis method and apparatus wherein the distortion of a sample eluting from the end of a capillary is reduced thereby resulting in enhanced detectability of an eluted sample.

REFERENCES

Dovichi et al., U.S. Pat. No. 5,439,578 (1995)
Grossman and Colburn, *Capillary Electrophoresis Theory and Practice,* Chapter 1, Academic Press (1992)
Grossman, U.S. Pat. No. 5,374,527 (1994)
Holman, *Heat Transfer,* Fourth Edition, McGraw-Hill (1976)
Madabhushi et al., U.S. Pat. No. 5,552,028 (1996)
Sambrook et al., eds., *Molecular Cloning: A Laboratory Manual,* Second Edition, Chapter 5, Cold Spring Harbor Laboratory Press (1989)
Takahashi et al., U.S. Pat. No. 5,529,679 (1996)

BACKGROUND

Electrophoretic separations of biopolymers and small molecules are critically important in modem biology and biotechnology, comprising an important component of such techniques as DNA sequencing, protein molecular weight determination, genetic mapping, and the like. A particularly preferred electrophoresis format is capillary electrophoresis (CE), where the electrophoresis is performed in a capillary tube having a small internal diameter. Capillary electrophoresis results in enhanced separation performance over traditional slab-based formats because the superior ability of the narrow-bore capillary to dissipate Joule heat allows for high electrical fields to be employed thereby resulting in fast separations in which sample diffusion is minimized.

In traditional CE systems, detection of a sample subsequent to separation is performed during electrophoresis while the sample is still located inside the capillary lumen. Thus, any excitation light required to excite the sample and any emission light coming from the sample must be transmitted through the wall of the capillary. A drawback of this approach is that the fused silica capillaries typically used in CE are poor optical elements, i.e., they cause significant scattering of light. Problems associated with light scattering are particularly problematic when it is desired to detect fluorescence from samples located in a plurality of closely-spaced capillaries by fluorescence because the scattered excitation light form one capillary will interfere with the detection of samples in neighboring capillaries.

One approach to solving the problem of on-capillary detection has been to detect a sample after the sample emerges from the capillary in a detection cell having superior optical characteristics, e.g., a flat quartz chamber. In one class of these systems, a "sheath flow" of liquid is used to transport the sample from the outlet of the CE capillary to a detection zone at which detection of the sample takes place (Takahashi; Dovichi). A drawback of sheath flow systems is that in order to avoid distortion of a sample zone in the detection cell, precise control of the flow rate of the sheath flow liquid is required. A second drawback of sheath flow systems is that the pressure used to drive the flow of the sheath flow liquid can cause back flow of the separation medium in the separation capillary thereby impacting resolution.

In another class of off-capillary detection systems, a sample zone is transported from the outlet of a CE capillary to a detection zone located in a detection cell by electrophoresis under the influence of the same voltage difference used to conduct the electrophoretic separation (Takahashi). However, because of the larger cross-sectional area of the detection cell as compared to the lumen of the capillary, the electric field diverges at the capillary outlet causing a distortion of an eluted sample zone. Such distortion results in severe loss of spatial resolution between adjacent sample zones eluting from a single capillary and/or between zones eluting from adjacent capillaries. This loss of spatial resolution tends to reduce the detectability of neighboring sample zones. As illustrated in FIG. 1, when distorted sample zones 52 and 53 eluting from capillary lumens 54 and 56 are interrogated by a light beam 51 having dimensions larger than the distorted sample zones in the direction of migration, it is impossible to independently detect the adjacent sample zones 52 and 53.

SUMMARY

The present invention is directed towards the discovery of a system for electrophoretically transporting a sample zone from an outlet of a capillary electrophoresis capillary to a detection zone separate from the capillary where the distortion of the eluted sample zone is reduced, thereby enhancing the detectability of neighboring sample zones. The zone distortion is reduced by controlling the divergence of the electric field at the outlet of the capillary by placing one or more "focusing" electrodes in the vicinity of the capillary outlet. The system finds particular application in automated polynucleotide sequencing systems employing fluorescence detection and a plurality of capillary electrophoresis tubes.

It is an object of the invention to provide a system for detecting a sample zone after separation by CE wherein the wall of the CE capillary does not interfere with the optical detection of the sample zone.

It is another object of the invention to provide a system for transporting a sample zone from an outlet of a capillary electrophoresis capillary to a detection zone separate from the capillary wherein a sheath flow is not required.

It is yet another object of the invention to provide a system for electrophoretically transporting a sample zone from an outlet of a capillary electrophoresis capillary to a detection zone separate from the capillary wherein distortion of the sample zone at the outlet of the capillary caused by the divergence of an electric field at the capillary outlet is reduced.

It is another object of the invention to provide a system for electrophoretically transporting a sample zone from an outlet of a capillary electrophoresis capillary to a detection zone separate from the capillary wherein sample zones eluting from neighboring capillaries do not interfere with one another.

The foregoing and other objects of the invention are achieved by an electrophoresis apparatus including one or more separation capillaries, each separation capillary having an inlet end and an outlet end; a first electrode in electrical communication with the inlet ends of the separation capillaries; a second electrode in electrical communication with the outlet ends of the separation capillaries; and one or more focusing electrodes in electrical communication with the outlet ends of the separation capillaries. In a preferred embodiment, the outlet ends of the capillaries are located in a detection cell. Optionally, the apparatus further includes a detector for detecting the sample after elution from the separation capillaries, e.g., a CCD detector, and a light source for exciting fluorescence of an eluted sample zone, e.g., a laser.

In a second aspect, the present invention includes methods of using the above-described apparatus.

These and other objects, features, and advantages of the present invention will become better understood with reference to the following description, drawings, and appended claims.

DETAILED DESCRIPTION OF THE PREFERRED EMBODIMENTS

Figure 1:
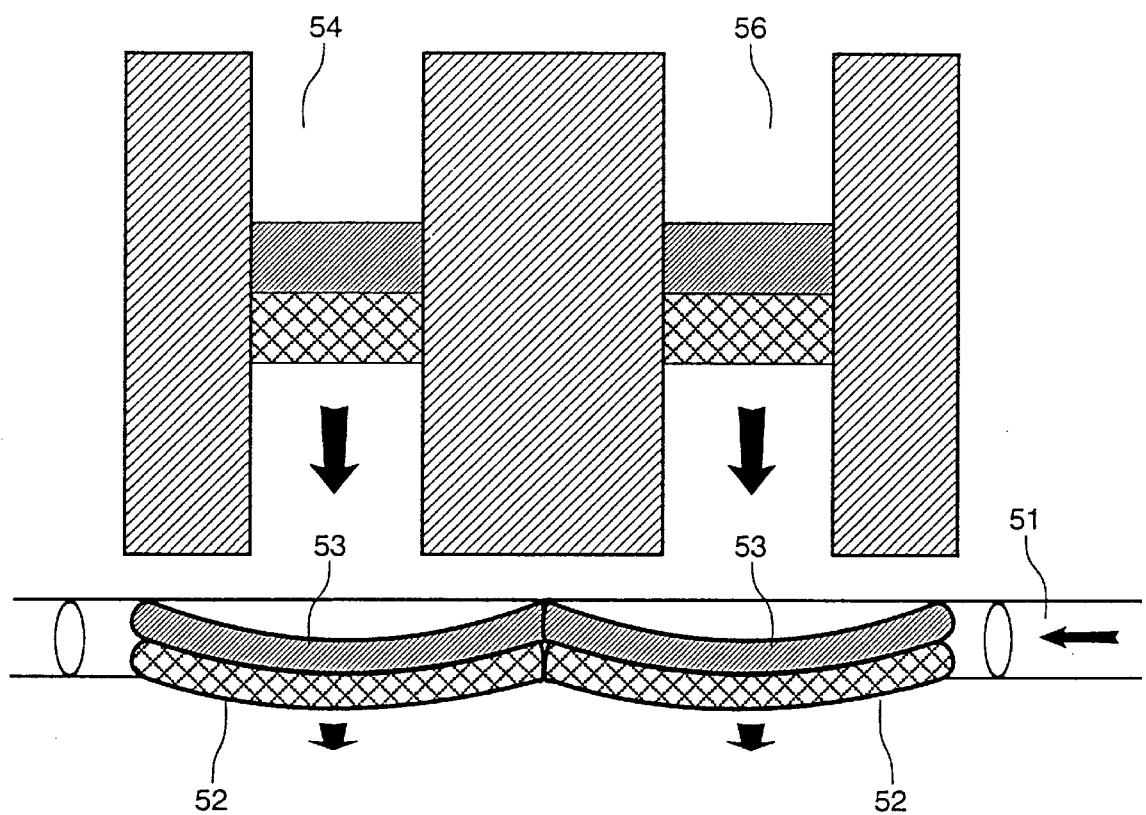
FIG. 1 depicts the distortion of sample zones eluting from a capillary caused by a diverging electrical field at a capillary outlet.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. Definitions

Unless stated otherwise, the following terms and phrases as used herein are intended to have the following meanings:

The term "capillary" as used herein refers to a tube or channel or other structure capable of supporting a volume of separation medium for carrying out electrophoresis. The geometry of a capillary may vary widely and includes tubes with circular, rectangular or square cross-sections, channels, groves, plates, and the like, and may be fabricated by a wide range of technologies. An important feature of a capillary for use with the invention is the surface-to-volume ratio of the surface in contact with the volume of separation medium. High values of this ratio permit better heat transfer from the separation medium during electrophoresis. Preferably, values in the range of about 0.4 to 0.04 are employed. These correspond to the surface-to-volume ratios of tubular capillaries with circular cross-sections having inside diameters in the range of about 10 $\mu$m to about 100 $\mu$m.

As used herein, the term "separation medium" refers to a medium in which an electrophoretic separation of sample components takes place. Separation media typically comprise several components, at least one of which is a charge-carrying component, or electrolyte. The charge-carrying component is usually part of a buffer system for maintaining the separation medium at a defined pH. Media for separating polynucleotides, proteins, or other biomolecules having different sizes but identical charge-frictional drag ratios in free solution, further include a sieving component. Such sieving component is typically composed of a cross linked polymer gel, e.g., cross linked polyacrylamide or agarose (Sambrook), or a polymer solution, e.g., a solution of polyacrylamide, hydroxyethyl cellulose, and the like (Grossman; Madabhushi).

As used herein, the term "sample zone" refers to a collection of molecules comprising a subset of sample components having similar electrophoretic migration velocities such that the molecules of a sample zone migrate as a defined zone. In the limit, a sample zone is made up of molecules having identical electrophoretic migration velocities.

As used herein, the term "zone distortion" refers to a change in the size, shape, and/or velocity of a sample zone upon moving from a lumen of a separation capillary into a detection cell having a larger cross sectional area. Such distortion includes compression and/or expansion of the zone in the direction of migration, and/or compression and/or expansion of the zone in a direction normal to the direction of electrophoretic migration.

II. The System

Figure 2:
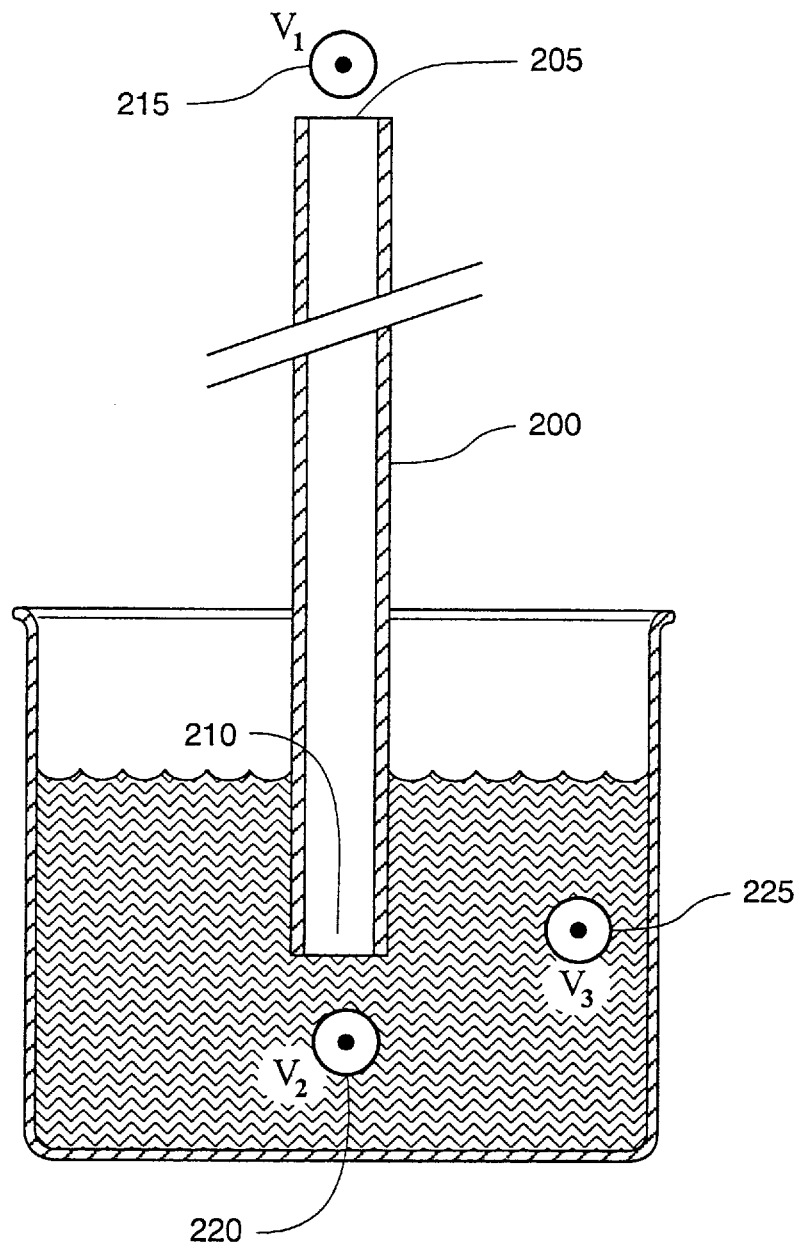
FIG. 2 shows a schematic diagram illustrating a device of the invention.

Generally, the present invention relates to a system for reducing the distortion of a sample zone eluting from a capillary electrophoresis separation capillary. The invention is based on the discovery that by placing one or more focusing electrodes in electrical communication with an outlet of a separation capillary, the divergence of an electrical field at a capillary outlet can be reduced, thereby reducing the distortion of sample zones eluted from the capillary. With reference to FIG. 2, the system includes one or more separation capillaries 200, each separation capillary having an inlet end 205 and an outlet end 210; a first electrode 215 in electrical communication with the inlet ends of the separation capillaries; a second electrode 220 in electrical communication with the outlet ends of the separation capillaries; and a focusing electrode 225 also in electrical communication with the outlet ends of the separation capillaries. In operation, the magnitude of the voltages of each of the electrodes are adjusted such that (i) the sample zone is transported from the inlet end to the outlet end of the separation capillaries and (ii) the distortion of the sample upon elution from the separation capillaries is reduced.

The electrical potential of the one or more focusing electrodes and the positioning of the focusing electrodes will depend on a number of factors including the shape of each of the focusing electrodes, the geometry of the detection cell, the electrical potential at the first and second electrodes, and the electrical resistance of the separation capillary.

When the first electrode is the anodic electrode, the magnitude of the voltage of the one or more focusing electrodes is preferably set such that the voltage is larger than the electrical potential at the outlet of the capillaries. Conversely, when the first electrode is the cathodic electrode, the magnitude of the voltage of the one or more focusing electrodes is preferably set such that the voltage is smaller than the electrical potential at the outlet of the capillaries. Preferably, the voltage of the one or more focusing electrodes is adjusted to avoid excessive Joule heating in a detection cell containing the electrodes.

The focusing electrode of the invention may be a single electrode, as shown in FIG. 2, or it may be made up multiple electrodes. For example, it might be desirable to ring a capillary outlet with a circular array of focusing electrodes.

The separation capillaries 200 used in the device of the invention may be any capillary as defined above. Preferably, the separation capillaries are made from an electrically insulating material, e.g., fused silica, quartz, silicate-based glass, such as borosilicate glass, phosphate glass, alumina-containing glass, and the like, or other silica-like materials. In addition, because the samples are detected outside of the separation capillary, non-optically clear materials may be used to form the capillaries, e.g., polymeric materials such as Teflon, silicone, and the like. In practice, the separation capillaries of the invention contain a separation medium to effect the electrophoretic separation of the components of the sample. Preferably the separation medium is a flowable noncrosslinked polymer solution having a viscosity of below about 500 cp.

Figure 3:
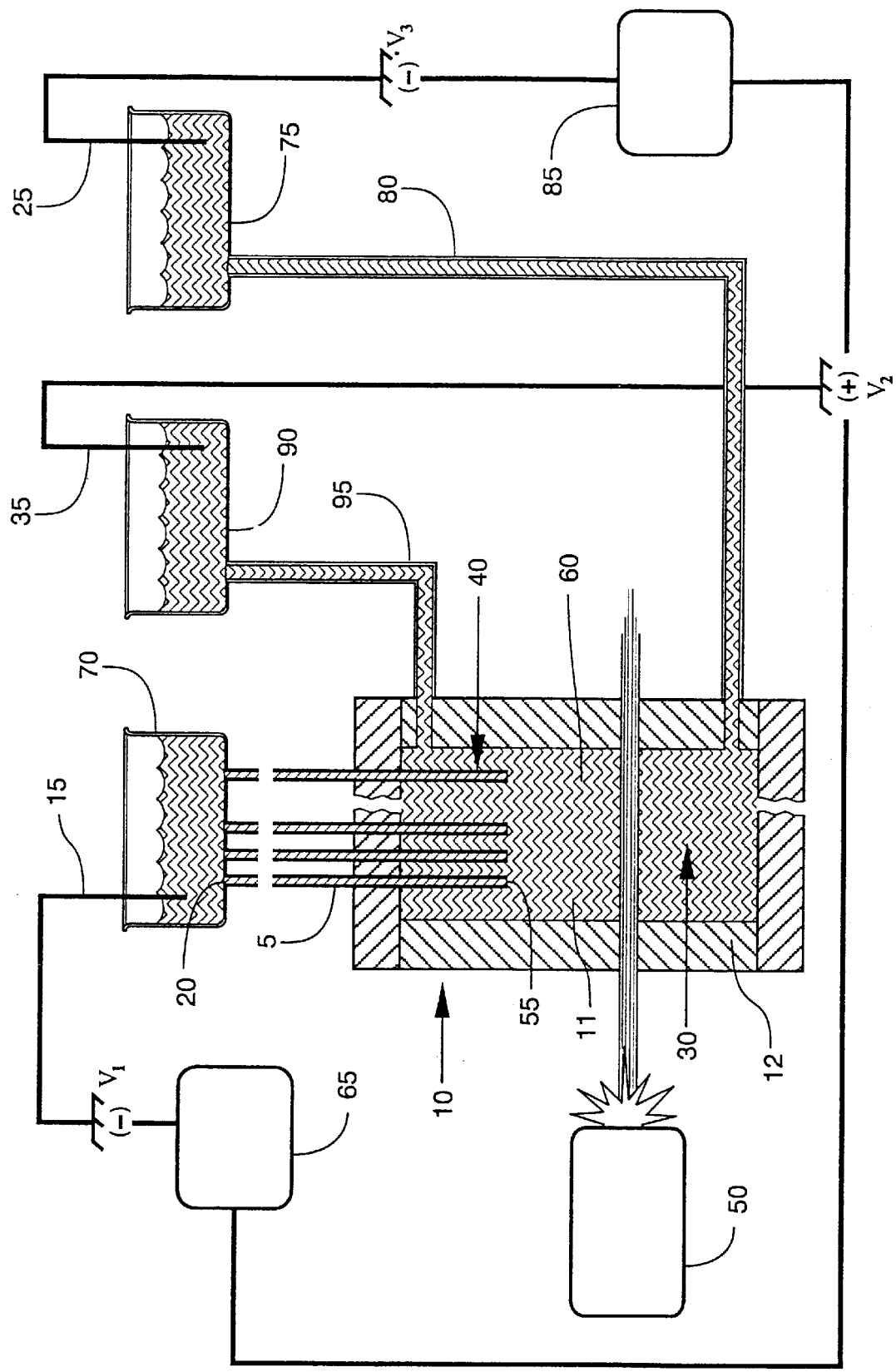
FIG. 3 shows a schematic diagram illustrating a preferred multicapillary device of the invention.

FIG. 3 shows a preferred embodiment of the system of the invention including multiple separation capillaries. Generally, the apparatus comprises one or more separation capillaries 5, a detection cell 10 housing outlet ends 55 of the capillaries, a first electrode 15 in electrical communication with an inlet end 20 of the separation capillaries, a second electrode 25 in electrical communication with a bottom portion 30 of the detection cell, and a focusing electrode 35 in electrical communication with a top portion 40 of the detection cell. In addition, the apparatus optionally includes a detector (not shown) for detection of sample zones eluting from the capillaries and a light source 50 for stimulating emission of the sample zones.

The first electrode 15 is in electrical communication with the inlet end 20 of the separation capillaries 5. During operation of the device, the first electrode is maintained at a first voltage $V_1$ using a first power supply 65. Preferably, the first electrode is physically isolated from the capillary inlets in order to prevent bubbles formed at the surface of the electrode from entering the capillaries or otherwise disrupting the electrophoresis. Electrical communication between the first electrode and the inlet ends of the separation capillaries is established by placing both the inlet ends of the capillaries and the first electrode in a first electrode reservoir 70, the reservoir being filled with an electrically conductive solution.

The second electrode 25 is in electrical communication with the detection cell which is itself in electrical communication with the outlet ends 55 of the separation capillaries 5. During operation of the device, the second electrode is maintained at a second voltage $V_2$ also using the first power supply 65. Preferably, electrical communication between the second electrode and the detection cell is established by placing the second electrode in a second electrode reservoir 75, the reservoir being in electrical communication with the bottom portion of the detection cell through a first conduit 80, both the second electrode reservoir and the first conduit being filled with an electrically conductive solution.

The focusing electrode 35 is in electrical communication with the detection cell which is itself in electrical communication with the outlet ends 55 of the separation capillaries 5. During operation of the device, the focusing electrode is maintained at a third voltage $V_3$ preferably using a second power supply 85. Preferably, electrical communication between the focusing electrode and the detection cell is established by placing the focusing electrode in a third electrode reservoir 90, the reservoir being in electrical communication with the detection cell through a second conduit 95, both the third electrode reservoir and the second conduit being filled with an electrically conductive solution.

The electrodes used in the device may be formed from any electrically conducting materials. Preferably, the electrodes are made from a chemically inert material, e.g., platinum, palladium, and the like. More preferably, the electrodes are made from a material which minimizes formation of gasses at the electrode surface, e.g., palladium.

The electrically conductive solution used to establish electrical continuity throughout the system may be any fluid capable of transporting an electrical current. Preferably, the conductive solution is an ionic solution, e.g., an aqueous solution containing a dissolved salt. The ionic strength of the solution is preferably chosen to be high enough to mask ion depletion of the solution in the vicinity of the electrodes, but not so high as to cause excessive Joule heating. Such Joule heating is particularly disadvantageous in the detector cell where thermal convection may lead to mixing of neighboring sample zones. Preferably, the conductive solution includes a buffer for stabilizing the pH of the solution. More preferably, the ionic composition of the conductive solution is the same in the separation capillaries, each of the electrode reservoirs, and the detector cell.

Preferably, the first, second, and third electrode reservoirs are located at the same elevation such that there is no pressure difference established across the detection cell or across the separation capillaries. In addition, it is desirable to vent each of the electrode reservoirs to atmosphere to avoid any pressure build-up in the system due to solvent degassing and/or temperature variation. Any pressure-driven flow through the separation capillaries can result in a severe loss of resolution due to the resulting parabolic flow profile, while any such flow through the flow cell can result in distortion and/or dilution of an eluted sample zone.

The detection cell 10 may be fabricated from any suitable electrically insulating material, e.g., glass, plastic, ceramic, and the like. Preferably, to facilitate optical detection of eluted sample zones, part or all of the front face 11 of detection cell 10 is formed from a material which efficiently transmits light, e.g., glass, quartz, and the like. In addition, to facilitate the introduction of an excitation light beam 51 into the detection cell to excite fluorescence of the sample zones, part or all of the left wall 12 of the detection cell is also formed from a material which efficiently transmits light. Preferably, the light-transmitting material does not significantly scatter light and has little intrinsic fluorescence. In a particularly preferred embodiment, the inside surfaces of the detector cell do not support electroosmotic flow in the presence of an ionic solution and an electric field, e.g., they are coated with an electroosmotic suppression agent (Madabhushi).

The device shown in FIG. 3 further includes a detector (not shown) for detecting the sample zones eluted into the detection zone 60 of the detection cell 10. The detector may be any type of detector for detecting emission of or absorbance of any type radiation, e.g., radioactivity, fluorescence, UV absorbance, and the like. Preferably the detector is capable of detecting fluorescence from a plurality of locations independently and simultaneously, e.g., a CCD camera, an array of photomultiplier tubes, a diode array, and the like. The detector is connected to a computer to store, analyze, and display data collected by the detector and/or to control the operation of the detector.

When fluorescence is used to detect the sample zones, the device also includes a light source 50 for exciting the fluorescence. In a preferred embodiment of the device the light source is a laser, e.g., an argon ion laser, a frequency-doubled solid state laser, and the like.

III. Examples

The invention will be further clarified by a consideration of the following examples, which are intended to be purely exemplary of the invention and not to in any way limit its scope.

Example 1

Finite Difference Simulation of an Electrical Field At A Capillary Outlet Located In a Detection Cell To better understand the effect of focusing electrodes in the present invention, the electric field at a capillary outlet was modeled using the Gauss-Seidel finite difference method (Holman).

Figure 4:
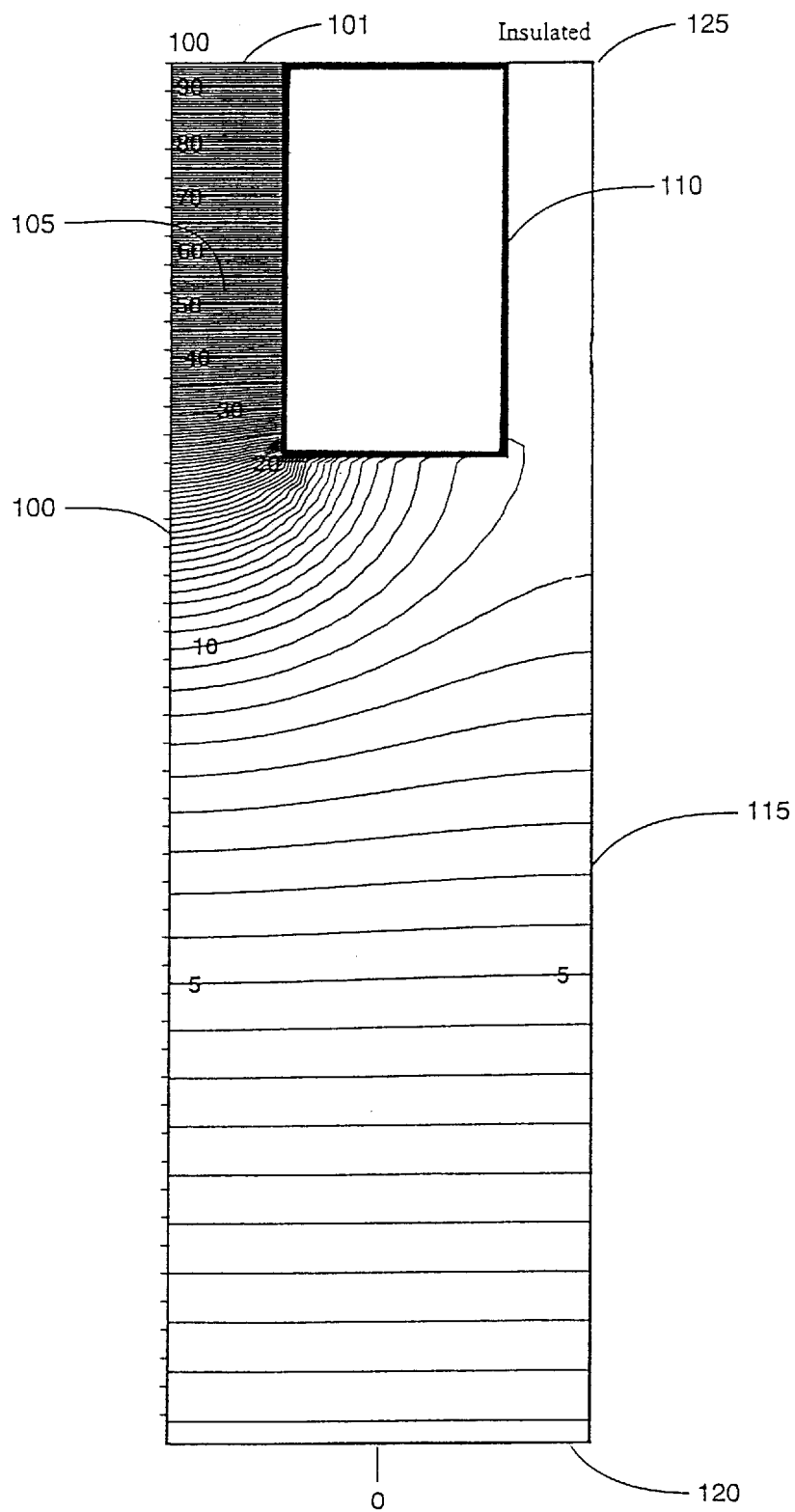
FIG. 4 shows the results of a finite difference simulation of an electric field in a detection cell not incorporating a focusing electrode.
Figure 5:
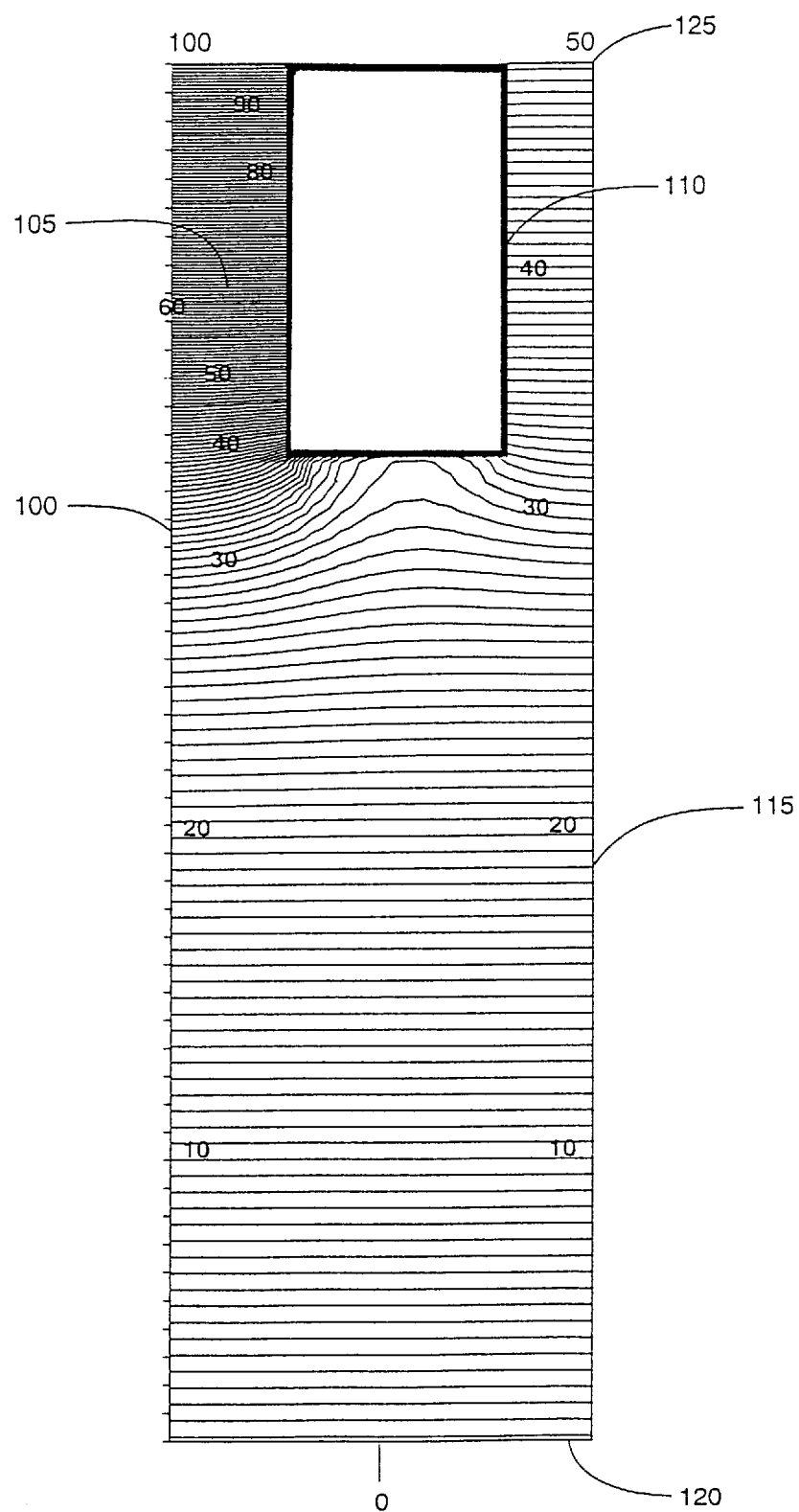
FIGS. 5 and 6 show the results of a finite difference simulation of an electric field in a detection cell incorporating a focusing electrode located at an upper surface of the detection cell at two different values of a focusing electrode voltage.
Figure 6:
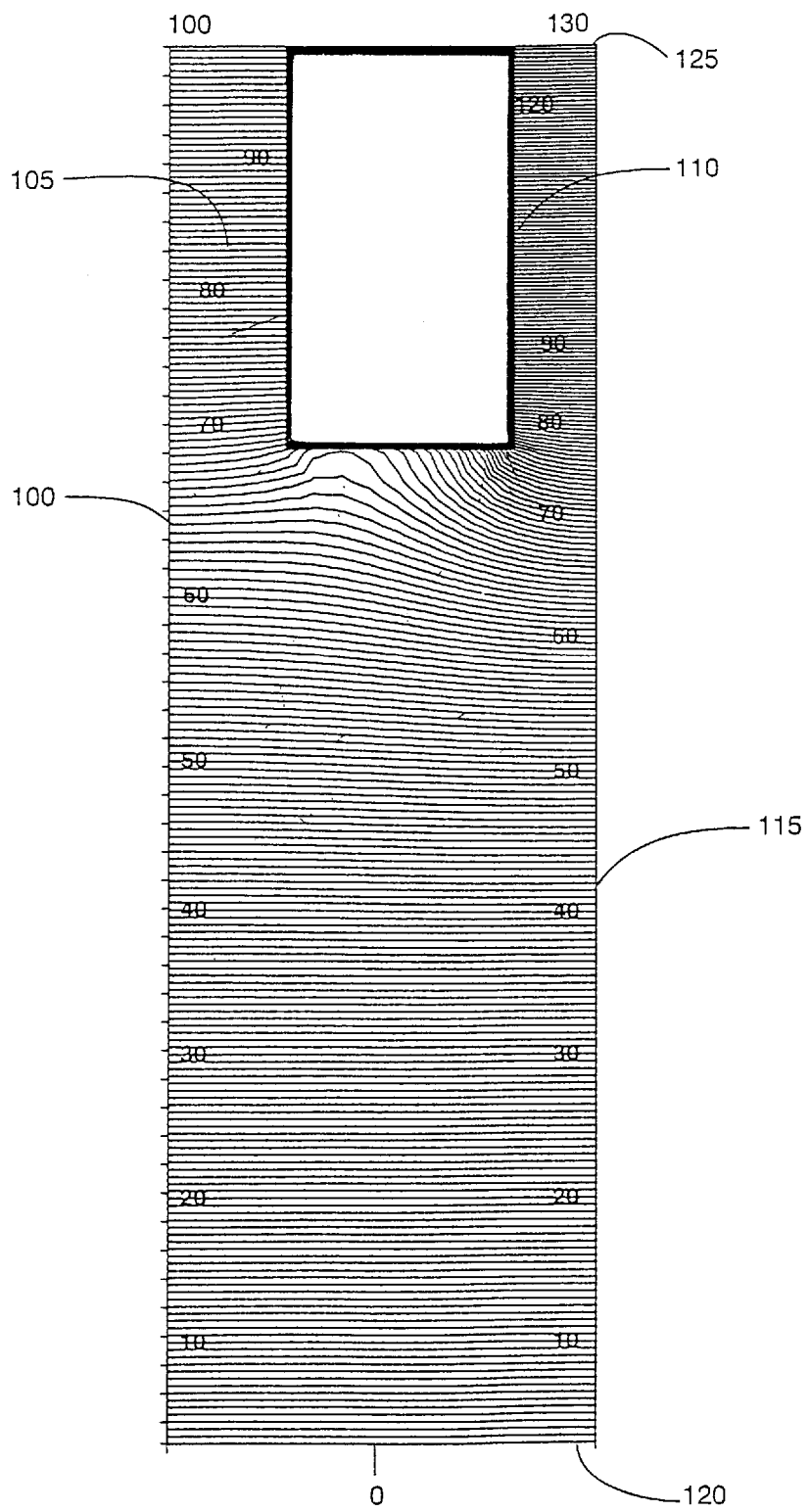

FIGS. 4–6 show the results of a finite difference simulation of an electric field at a capillary outlet located in a detection cell for various focusing electrode voltages. The figure shows in cross section the centerline 100 of a separation capillary, the capillary lumen 105, the wall 110 of the capillary, and the side 115, bottom 120, and top 125 walls of a detection cell. The horizontal lines in the figure represent lines of equal electrical potential, i.e., isopotential contours. The dimensions used in the simulation were as follows: the radius of the capillary lumen was 25 µm, the capillary wall was 35 µm thick, the distance between the outer surface of the capillary and the side wall of the detection cell was 20 µm, the length of the capillary section was 70 µm, and the distance from the outlet of the capillary to the bottom wall of the detection cell was 180 µm. The capillary wall was assumed to be an insulator and the electrical conductivity of the separation medium filling the capillary lumen and the detection cell was assumed to be 0.1 $\Omega^{-1}$ $m^{-1}$. The electrical potential at the bottom wall 120 of the detection cell was set at 0 units, corresponding to $V_2$ in FIG. 2, and the side wall of the detection cell 115 was assumed to be an insulator. (Note that arbitrary units for electrical potential were used in the simulation.) The electrical potential at the capillary inlet 101 was set at 100 units, corresponding to $V_1$ in FIG. 2, and the electrical potential of the top 125 wall of the detection cell, corresponding to $V_3$ in FIG. 2, was varied in each of the simulations shown in the figures.

In the simulation shown in FIG. 4, the top wall 125 of the detection cell was made to be an insulator. This situation corresponds to a detection cell having no focusing electrode. As can be seen in the figure, upon exiting the capillary lumen, the isopotential contours diverge. Given that a charged molecule will travel in a direction perpendicular to the isopotential contours, these curved isopotential contours indicate that a sample zone leaving the capillary under these conditions would be substantially distorted.

FIG. 5 shows the results of a simulation essentially the same as that shown in FIG. 4, the only difference being that here the electrical potential at the top wall of the detection cell 125 was set to a value of 50 units. This corresponds to setting the third electrode in the device shown in FIG. 2 to a potential of 50 units. Here, the divergence of the isopotential counters exiting the capillary is less pronounced, indicating that a sample zone exiting the capillary would be somewhat less distorted than in the simulation shown in FIG. 4.

FIG. 6 shows the results of a simulation essentially the same as that shown in FIGS. 4 and 5, the only difference being that here the electrical potential at the top wall 125 of the detection cell was set a value of 130 units. This corresponds to setting the third electrode in the device shown in FIG. 2 to a potential of 130 units. Here, the curvature of the isopotential contours exiting the capillary are essentially flat, indicating that a sample zone would exit the capillary without significant distortion.

All publications and patent applications referred to herein are hereby incorporated by reference to the same extent as if each individual publication or patent application was specifically and individually indicated to be incorporated by reference.

Although only a few embodiments have been described in detail above, those having ordinary skill in the electrophoresis art will clearly understand that many modifications are possible in the preferred embodiment without departing from the teachings thereof all such modifications are intended to be encompassed within the following claims.

I claim:

1. An electrophoresis apparatus comprising:

one or more separation capillaries, each separation capillary having an inlet end and an outlet end;

a first electrode in electrical communication with the inlet ends of the separation capillaries;

a second electrode in electrical communication with the outlet ends of the separation capillaries;

one or more focusing electrodes in electrical communication with the outlet ends of the separation capillaries;

a detection cell housing the outlet ends of the separation capillaries; and a detector for detecting a sample located in the detection cell after elution from a separation capillary.

2. The apparatus of claim 1 wherein the detector is a charge coupled device.

3. The apparatus of claim 1 further including a light source for exciting fluorescence of the sample in the detection cell.

4. The apparatus of claim 3 wherein the light source is a laser.

5. A method for reducing the distortion of a sample zone eluting from a capillary electrophoresis capillary comprising the steps of:

providing one or more separation capillaries, each separation capillary having an inlet end and an outlet end;

providing a first electrode in electrical communication with the inlet ends of the separation capillaries;

providing a second electrode in electrical communication with the outlet ends of he separation capillaries; and providing one or more focusing electrodes in electrical communication with the outlet ends of the separation capillaries;

adjusting the voltage of each of the electrodes such that (i) the sample zone is transported from the inlet end to the outlet end of the separation capillaries and (ii) the distortion of the sample zone eluting from the separation capillaries is reduced.

6. The method of claim 5 further including providing a detector for detecting the sample after elution from the separation capillaries.

7. The method of claim 6 wherein the detector is a charge coupled device.

8. The method of claim 5 further including providing a light source for exciting fluorescence of an eluted sample zone.

9. The method of claim 5 wherein the light source is a laser.

\* \* \* \* \*